US006738874B2

(12) United States Patent
Zsohar

(10) Patent No.: US 6,738,874 B2
(45) Date of Patent: May 18, 2004

(54) CONTROLLER ARCHITECTURE AND STRATEGY FOR SMALL DISCONTIGUOUS ACCESSES TO HIGH-DENSITY MEMORY DEVICES

(75) Inventor: Leslie Zsohar, Austin, TX (US)

(73) Assignee: Layer N Networks, Inc., Austin, TX (US)

( * ) Notice: Subject to any disclaimer, the term of this patent is extended or adjusted under 35 U.S.C. 154(b) by 42 days.

(21) Appl. No.: 10/078,253

(22) Filed: Feb. 16, 2002

(65) Prior Publication Data

US 2002/0194445 A1 Dec. 19, 2002

Related U.S. Application Data

(60) Provisional application No. 60/326,250, filed on Oct. 1, 2001, provisional application No. 60/326,251, filed on Oct. 1, 2001, provisional application No. 60/326,252, filed on Oct. 1, 2001, provisional application No. 60/326,266, filed on Oct. 1, 2001, provisional application No. 60/300,955, filed on Jun. 26, 2001, provisional application No. 60/300, 957, filed on Jun. 26, 2001, and provisional application No. 60/288,015, filed on May 2, 2001.

(51) Int. Cl.[7] .................................... G06F 12/00

(52) U.S. Cl. .................... 711/157; 711/158; 711/168; 711/169

(58) Field of Search ............................ 711/157, 158, 711/168, 169

(56) References Cited

U.S. PATENT DOCUMENTS

| | | | | | |
|---|---|---|---|---|---|
| 4,799,149 | A | | 1/1989 | Wolf | |
| 5,542,061 | A | | 7/1996 | Omata | |
| 5,577,236 | A | * | 11/1996 | Johnson et al. | 713/400 |
| 5,699,537 | A | | 12/1997 | Sharangpani et al. | |
| 5,724,279 | A | | 3/1998 | Benaloh et al. | |
| 5,745,913 | A | * | 4/1998 | Pattin et al. | 711/105 |
| 5,764,554 | A | | 6/1998 | Monier | |
| 5,771,369 | A | * | 6/1998 | Curran | 711/105 |
| 5,784,582 | A | * | 7/1998 | Hughes | 710/117 |
| 5,787,457 | A | * | 7/1998 | Miller et al. | 711/105 |
| 5,983,299 | A | | 11/1999 | Qureshi | |
| 5,987,574 | A | | 11/1999 | Paluch | |
| 6,088,453 | A | | 7/2000 | Shimbo | |
| 6,134,244 | A | | 10/2000 | Van Renesse et al. | |
| 6,141,705 | A | | 10/2000 | Anand et al. | |
| 6,151,393 | A | | 11/2000 | Jeong | |
| 6,157,955 | A | | 12/2000 | Narad et al. | |
| 6,341,299 | B1 | | 1/2002 | Romain | |
| 6,591,350 | B1 | * | 7/2003 | Stenfort | 711/158 |

OTHER PUBLICATIONS

Menezes, A.J., et al "Handbook of Applied Cryptography" Boca Raton, CRC Press, 1997.

Kornerup, P., "High–Radix Modular Multiplication for Crytosystems" Department of Mathematics and Computer Science, (1993), pp. 277–283.

Sunar, B. and KOC, C.K., "An Efficient Optimal Normal Basis Type II Multiplier" Brief Contributions, IEEE Transactions on Computers, vol. 50, No. 1, (Jan. 2001), pp. 83–87.

KoC, C.K., "Comments on 'Residue Arithmetic VLSI Array Architecture for Manipulator Pseudo–Inverse Jacobian Computation'" Communications, IEEE Transactions on Robotics and Automation, vol. 7, No. 5, (Oct. 1991), pp. 715–716.

Savas, E. and Koc, C.K., "The Montgomery Modular Inverse–Revisted" IEEE Transactions on Computers, vol. 49, No. 7, (Jul. 2000), pp. 763–766.

(List continued on next page.)

*Primary Examiner*—Matthew Kim
*Assistant Examiner*—Stephen Elmore
(74) *Attorney, Agent, or Firm*—Hulsey Grether & Fortkort, LLP; Aaron A. Weiss

(57) ABSTRACT

A RAM device including a memory and a memory controller. The memory controller can be configured to buffer incoming requests, prioritize the requests into a final order, and submit the requests to the memory in the final order. The final order, as needed, is selected to maximize overlap of incoming requests' timing cycles.

10 Claims, 5 Drawing Sheets

OTHER PUBLICATIONS

Walter, C.D., "Montgomery's Multiplication Technique: How to Make it Smaller and Faster" in Cryptographic Hardware and Embedded Systems—CHAS 1999, C. Paar (Eds.) K. Ko, Ed. 1999, Springer, Berlin Germany, pp. 61–72.

Oh, H. and Moon, J., "Modular Multiplication Method" IEE Proc.–Comput. Digit. Tech., vol. 145, No. 4, (Jul. 1998), pp. 317–318.

Blum, T., "Modular Exponentiation on Reconfigurable Hardware" Master's thesis, ECE Department, Worcester Polytechnic Institute, Submitted to Faculty Apr. 8, 1999, Published May 1999. Retrieved from the Internet <URL: http://www.wpi.edu/pubs/ETD/Available/etd–090399–090413/unrestricted/blum.pdf>.

Marwedel, P., et al. "Built in Chaining: Introducing Complex Components into Architectural Synthesis." Apr. 1996. Proceedings of the ASP–DAC, 1997. [online]. Retrieved from the Internet <URL:http://eldorado.uni–dortmund.de.8080/FB4/Is12/forshung/1997/aspdac/aspacPDF>.

Tiountchik, A., and Trichina, E., "RSA Acceleration with Field Programmable Gate Arrays" Lecture Notes in Computer Science, vol. 1587, pp. 164–176. Retrieved from the Internet:<URL:http://citeseer.nj.nec.com/274658.html>.

Menezes, A.J., et al "Efficient Implementation" from the-Handbook of Applied Cryptography, (Boca Raton, CRS Press, 1997), pp. 591–607.

Dimitrov, V. and Cooklev, T., "Two Algorithms for Modular Exponentiation Using Nonstandard Arithmetics" IEICE Trans. Fundamentals, vol. E78–A, No. 1, Jan. 1995.

Koc, C.K. and Hung, C.Y., "Carry–Save Adders for Computing the Product AB Modulo N" Electronics Letters, vol. 26, No. 13, (Jun. 21, 1990), pp. 899–900.

Freking, W. L. and Parhi, K.K., "Montgomery Modular Multiplication and Exponentiation in the Residue Number System" Proc. 33rd Asilomar Conf. Signals Systems and Computer, Oct. 1999, pp. 1312–1316.

Tenca, A.F. and Koc, C.K., "A Scalable Architecture for Montgomery Multiplication" in: Koc, C.K. and Paar, C. Cryptographic Hardware and Embedded Systems, CHES 99, Lecture Notes in Computer Science, No. 1717. 1998, New York, NY: Springer–Verlog, 1999.

Koc, C.K. and Acar, T., "Montgomery Multiplication in GF (2k)" 3rd Annual Workshop on Selected Areas in Cryptography, (Aug. 15–16, 1996), pp. 95–106.

Bajard, J.C., et al "An RNS Montgomery Modular Multiplication Algorithm" IEEE Transactions on Computer, vol. 47, No. 7, (Jul. 1998), pp. 766–776.

Eldridge, S.E., "A Faster Modular Multiplication Algorithm" International Journal of Computer Math, vol. 40, (1991), pp. 63–68.

Bossalaers, A.., et al "Comparison of Three Modular Reduction Functions" In Douglas R. Stinson, editor, Advances in Cryptology—CRYPTO '93, vol. 773 of Lecture Notes in Computer Science, (Aug. 22–26, 1993), pp. 166–174.

Montgomery, P.L., "Modular Multiplication Without Trial Division" Mathematics of Computation, vol. 44, No. 170 (Apr. 1985), pp. 519–521.

Koc, C.K., et al "Analyzing and Comparing Montgomery Multiplication Algorithms" IEEE Micro, vol. 16, Issue 3, (Jun. 1996), pp. 26–33.

* cited by examiner

CONTROLLER ARCHITECTURE AND STRATEGY FOR SMALL DISCONTIGUOUS ACCESSES TO HIGH-DENSITY MEMORY DEVICES

CROSS-REFERENCE TO RELATED APPLICATIONS

This application claims the benefit of the following U.S. Provisional Applications, all of which are hereby incorporated by reference, and the content of which are not necessarily identical to the content of this application:

COMMONLY OWNED AND PREVIOUSLY FILED U.S. PROVISIONAL PATENT APPLICATIONS

| Atty. Dkt. # | Serial Number | Title | Filing Date |
|---|---|---|---|
| 501143.000005 | 60/288,015 | Method and Apparatus for Shotgun Multiplication and Exponentiation | May 2, 2001 |
| 501143.000010 | 60/300,957 | Method and Residue Calculation Using Casting Out | June 26, 2001 |
| 501143.000011 | 60/300,955 | Add-Drop Layer 3 Ethernet Ring Switch | June 26, 2001 |
| 501431.000014 | 60/326,266 | Application Specific Information Processing System | October 1, 2001 |
| 501143.000015 | 60/326,252 | Efficient Use of DRAM-Based Devices For Small Discontiguous Memory Accesses | October 1, 2001 |
| 501143.000016 | 60/326,251 | Exponentiation Engine | October 1, 2001 |
| 501143.000017 | 60/326,250 | Method for Squaring | October 1, 2001 |

The current application shares some specification and figures with the following commonly owned and concurrently filed applications, all of which are hereby incorporated by reference:

COMMONLY OWNED AND CURRENTLY FILED U.S. NONPROVISIONAL PATENT APPLICATIONS

| Atty. Dkt. # | Serial Number | Title | Filing Date |
|---|---|---|---|
| 501143.000024 | 10/078,252 | Computational Method, System, and Apparatus | Feb. 16, 2002 |

The current application shares some specification and figures with the following commonly owned and previously filed applications, all of which are hereby incorporated by reference:

COMMONLY OWNED AND PREVIOUSLY FILED U.S. NONPROVISIONAL PATENT APPLICATIONS

| Atty. Dkt. # | Serial Number | Title | Filing Date |
|---|---|---|---|
| 501143.000008 | 10/068,294 | Ring Arithmetic Method, System, and Apparatus | Feb. 5, 2002 |
| 501143.000019 | 10/068,295 | Application-Specific Information-Processing Method, System, and Apparatus | Feb. 5, 2002 |

The benefit of 35 U.S.C. §120 is claimed for all of the above referenced commonly owned applications. The contents of the applications referenced in the tables above are not necessarily identical to the contents of this application.

All references cited hereafter are incorporated by reference to the maximum extent allowable by law. To the extent a reference may not be fully incorporated herein, it is incorporated by reference for background purposes and indicative of the knowledge of one of ordinary skill in the art.

BACKGROUND OF THE INVENTION

1. Field of the Invention

The present invention relates generally to an information-processing system and in particular to an information-processing system with high-density memory.

2. Description of Related Art

For purposes of the present discussion, RAM devices may be divided into at least two general classes based on intended applications and cost/performance tradeoffs.

A first class (type one RAM) is comprised of devices whose design is optimized for high-density and access to large amounts of contiguous data, while a second class (type two RAM) is comprised of devices whose design is optimized for random access to small amounts of data that may be discontiguous within the total address space of the memory.

An example of type one RAM is Dynamic RAM (DRAM), which by definition includes Synchronous DRAM (SDRAM) and Double Data Rate Synchronous DRAM (DDR-SDRAM). Type one RAM memory cells may be packed relatively densely, so the large quantity of data that can be stored in such devices allows the cost per data unit stored to be minimized. Such devices are a typical choice for providing large amounts of memory in systems that require this. Since the performance of most such systems benefit from rapid access to large contiguous blocks of data, the designs are optimized to enable this, at the cost of providing relatively slower access to small blocks of discontiguous data. Such a design tradeoff is often appropriate because many business, scientific, engineering and graphics data processing applications have the characteristic of operating on relatively large blocks of contiguous data.

Static RAM (SRAM) is one example of type two RAM. Type two RAM memory cells cannot be packed as densely as type one RAM memory cells and dissipate more power than type one RAM memory cells. The consequence of the relatively low packing density and the higher power of type two RAM is that the quantity of data that can be stored is lower than type one RAM devices would provide and a higher cost per unit data stored. Current design practice is to accept this higher cost in order to gain uniformly low access latency over the total address space of the memory.

Certain data processing applications such as networking components inevitably need to operate on discontiguous data. The current design practice yields acceptable cost-effectiveness provided the quantity of memory which must be provided is relatively low, since the aggregate of the higher cost per data unit of the memory remains a low portion of the total system cost. But for systems requiring large amounts of memory, type two RAM can be infeasible due to cost, and the high power consumption and low density of type two RAM can create heat dissipation and physical size problems. The growing processing and memory needs of networking components provide one example of this situation.

Network infrastructure speeds have increased dramatically, often generation-to-generation being 10X in throughput from the previous. Historically the infrastructure itself only required the information related to routing or other transient data/statistics to be maintained in the wire speed equipment. The servers themselves or other general purpose CPUs in equipment were responsible for the processing of persistent state such as TCP, UDP, IPSec or SSL connection information.

General purpose CPUs with traditional memory systems or even specialized processors for routing (i.e., stand-alone Network Processors) do not have the memory subsystems to handle both the high-data-throughput and the high-simultaneous-connection specifications required. The aggregation of services at the edge of a data center can require one million or more TCP connections for an application such as SSL or similarly 500,000+ security associations for IPSec. Firewalls, load balancers, etc. could also be enhanced if there were a capability to either terminate or shadow TCP connections at wire speeds. A "shadow TCP connection" is one that does not terminate the TCP connection, but maintains state with the connection so as to monitor the terminated TCP connection. It would be valuable to provide sufficient memory to support such tasks, but they inherently need to access small blocks of discontiguous data. The cost of providing adequate amounts of suitable memory using existing design precepts can make such systems infeasible due to total cost.

In light of the above discussion, it would be desirable to provide a memory architecture that enabled the use of the high-density, low power and low cost devices such as type one RAM, while providing adequately low latency in accessing small blocks of discontiguous data. The present invention solves this and other problems.

BRIEF SUMMARY OF THE INVENTION

In light of reviewing the prior art, it is desirable to provide a memory architecture strategy based on the use of high-density storage devices, providing low latency in accessing the full address space of the memory to write or read small blocks of discontiguous data.

A memory architecture design and strategy of the present invention uses memory devices that would normally be considered disadvantageous, but by accommodating the data input, output, and other peripheral controller services, overall performance in this mode is optimized. The surprising result is that even though the choice of memory is inappropriate for the task based on the precepts of the prior art, the overall memory system is effective.

One example of a normally disadvantageous situation that is beneficial in connection with one or more embodiments of the present invention is bank switching in DDR-SDRAM, thereby achieving feasibility without resort to, for example, SRAM.

BRIEF DESCRIPTION OF THE DRAWINGS

The following drawings form part of the present specification and are included to further demonstrate certain aspects of the present invention. The figures are not necessarily drawn to scale. The invention may be better understood by reference to one or more of these drawings in combination with the detailed description of specific embodiments presented herein.

DETAILED DESCRIPTION OF PREFERRED EMBODIMENTS

Figure 1:
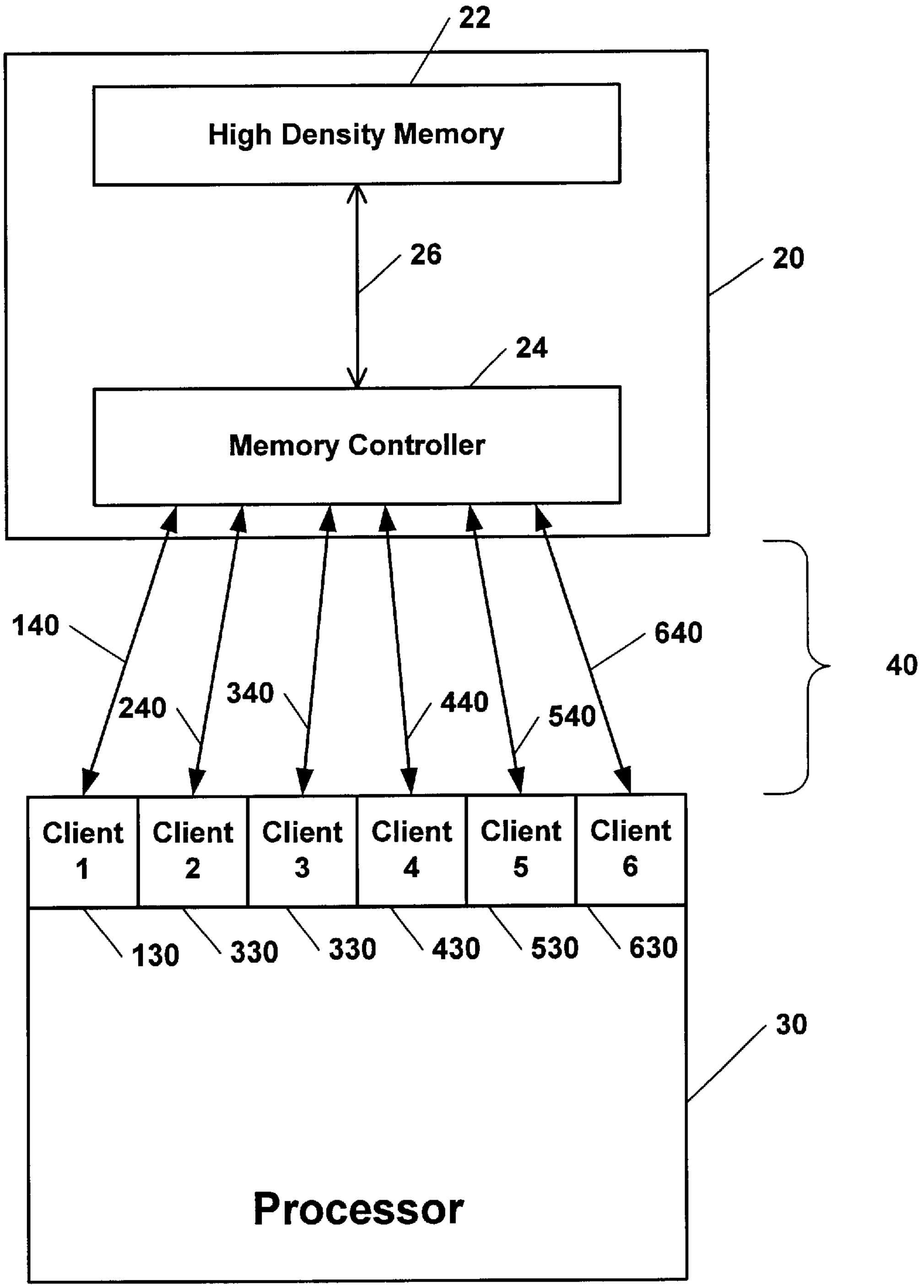
FIG. 1 is a block diagram of a memory subsystem and its data input and output connectivity in accordance with an embodiment of the present invention.

Referring now to FIG. 1, we describe the general configuration of a memory subsystem 20 in accordance with an embodiment of the present invention.

Memory subsystem 20 is composed of a high-density memory 22 and its associated memory controller 24, connected by data channel 26. Within the scope of the present invention, the data channel can be any appropriate communication technology.

The high-density memory 22 is type one RAM. The bit width of data channel 26 is matched to the address and data widths of the high-density memory 22. In this specific example data channel 26 is sixty-four bits wide, but in general its width is determined by the device chosen for high-density memory 22. Memory controller 24 receives and sends data from and to processor 30 over memory subsystem communication channel 40. In this embodiment, channel 40 is comprised of a plurality of smaller data channels 140, 240, 340, 440, 540, and 640, each of which transfers data from and to an individual processor client, 130, 230, 330, 430, 530, and 630. Within the scope of the present invention, there may be any number of processor clients. For clarity, processor clients may be any entity capable of sending a memory access request.

In this specific example subchannels 140, 240, 340, 440, 540, and 640 are chosen to be thirty-two bits wide, but in general this will depend on overall system design. In fact, specific design choices in various embodiments described in this application are meant to illustrate some embodiments of—not to limit the scope of—the present invention.

Figure 2:
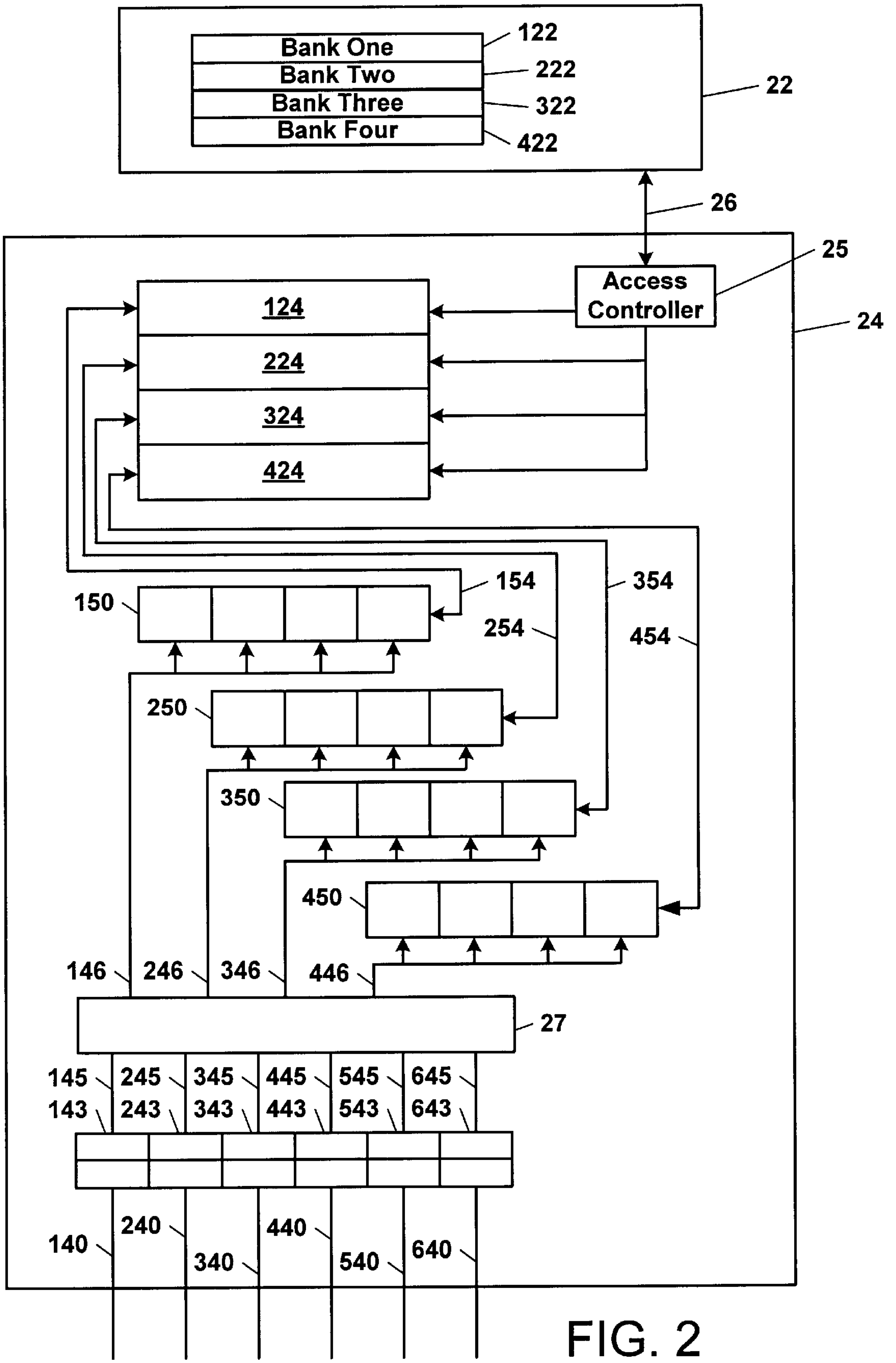
FIG. 2 is related to FIG. 1, and shows a block diagram of data buffering within the memory system of FIG. 1, in accordance with an embodiment of the present invention.

Referring now to FIG. 2, we describe in more detail the data buffering and operating sequence within memory controller 24.

The detailed design of memory controller 24 is determined by the specification of high-density memory unit 22. In this example, memory unit 22 is divided into four banks 122, 222, 322, and 422. Within the scope of the present invention, the memory unit 22 can have any number of banks.

An example of memory unit 22 is Micron Technology (Boise, Id., USA) part number MT46V64M4TG DDR SDRAM. Each of banks 122, 222, 322, and 422 contains memory cells within a specific address range, and there is no overlap between these ranges. Memory unit 24 has a sixty-four-bit data communication channel 26, which is used to communicate between high-density memory 22 and memory controller 24. Within the scope of the present invention, communication channel 26 can be any appropriate communication technology.

Memory controller 24 contains three groups of data buffers. Some embodiments will have different groupings of buffers, as is obvious to those of typical skill in the art.

In this embodiment, data is transferred only on a single edge of each clock cycle for communication channels other than channel 26. Thus, each of buffers 124, 224, 324 and 424 is 128 bits wide and communicates through access controller 25 such that only one of buffers 124, 224, 324, and 424 may access memory 22 via communication channel 26 at any given moment. Within the scope of the present invention, there may be any number of buffers such as 124, 224, 324, and 424. Typically, the number of buffers such as 124, 224, 324, and 424 will be equal to the number of memory banks such as 122, 222, 322, and 422.

Further, each of buffers 124, 224, 324, and 424 is in communication with only one of the buffers 150, 250, 350 and 450 over 128-bit wide channels 154, 254, 354 and 454. Within the scope of the present invention, there may be any number of buffers such as 150, 250, 350, and 450. Typically, the number of buffers such as 150, 250, 350, and 450 will be equal to the number of buffers such as 124, 224, 324, and 424. In some embodiments, the buffers 124, 224, 324, and 424 and the buffers 150, 250, 350, and 450 are combined into a single set of buffers.

This embodiment shows certain elements grouped in memory controller 24, but as with all of the particulars of this embodiment, those elements can be separated or further grouped with other elements of the embodiment without departing from the scope of the invention.

In this embodiment, memory controller 24 further includes a set of processor client buffers 143, 243, 343, 443, 543, and 643. Data channels 140, 240, 340, 440, 540, and 640 connect processor clients 130, 230, 330, 430, 530, and 630 with those client buffers on a one-to-one basis.

Each processor client buffer 143, 243, 343, 443, 543, and 643 has two buffer portions in this embodiment, each portion having capacity to buffer a single memory access request. In some embodiments, each client buffer has a different capacity, both in number of portions and in size of portions, and capacities of different client buffers in a single embodiment can vary.

In this embodiment, each processor client 130, 230, 330, 430, 530, and 630 has the ability to generate memory access requests only for a single bank. In the embodiment depicted in FIG. 2, the relationships are as follows:

processor client 1—buffer 143—bank one 122 processor client 2—buffer 243—bank two 222 processor clients 3 and 4—buffers 343 and 443—bank three 322 processor clients 5 and 6—buffers 543 and 643—bank four 422

Some embodiments do not limit the ability of each processor client buffer this way. One characteristic is that the embodiment as a whole recognizes when different memory access requests are directed to different memory banks so that the requests can be prioritized to improve the amount of overlap so as to reduce the total time to complete the accesses. Improvement of the overlap by similar mechanisms in other embodiments is contemplated. For example, an embodiment groups reads and writes together to improve memory access cycle overlap. Yet another embodiment groups reads and writes and also bank switches. The remaining discussion sets forth implementation details for bank switching. Similarly detailed discussions of other overlap-improvement mechanisms are obvious to those of ordinary skill in the art, so are not included in this application.

At a point in time, a snapshot is taken of the processor client buffers' 143, 243, 343, 443, 543, and 643 contents. Any four of the processor client buffers 143, 243, 343, 443, 543, and 643 can be selected for handling—one processor client for each buffer 150, 250, 350, and 450. This is because channels 145, 245, 345, 445, 545, and 645 are inputs to cross bar 27 such that any input can send to any output of cross bar 27. Channels 146, 246, 346, and 446 are outputs of cross bar 27. Thus, the request of any processor client can be sent to any of the buffers 150, 250, 350, and 450.

If four or fewer requests are in processor client buffers 143, 243, 343, 443, 543, and 643, then all the requests are processed. If more than four requests are in processor client buffers 143, 243, 343, 443, 543, and 643, then the requests are chosen for processing in order to improve overlapping of their memory access cycles—this embodiment maximizes memory-bank-diversity of the selected requests. Further, if there are two bank one requests and two bank two requests, they are sent in alternating order to buffers 150, 250, 350, and 450. Thus, one possible configuration would send a bank one request to buffer 150, a bank two request to buffer 250, the other bank one request to buffer 350, and the other bank two request to buffer 450. Then when the requests are eventually in buffers 124, 224, 324, and 424, their corresponding memory accesses will alternate between bank one 122 and bank two 222. In that way, three bank switches occur during the four memory bank accesses.

Channels 146, 246, 346, and 446 are thirty-two bits wide. Their thirty-two-bit-wide request components are assembled in buffers 150, 250, 350, and 450 into 128-bit-wide requests.

Within the scope of the present invention, the various buffers can have any capacity without departing from the scope of the invention. In some embodiments, the three sets of buffers discussed may be combined into a single set of buffers.

In various other embodiments, bank switching occurs non-sequentially, randomly, according to statistically determined rules, according to manually assigned rules, etc.

Figure 3A:
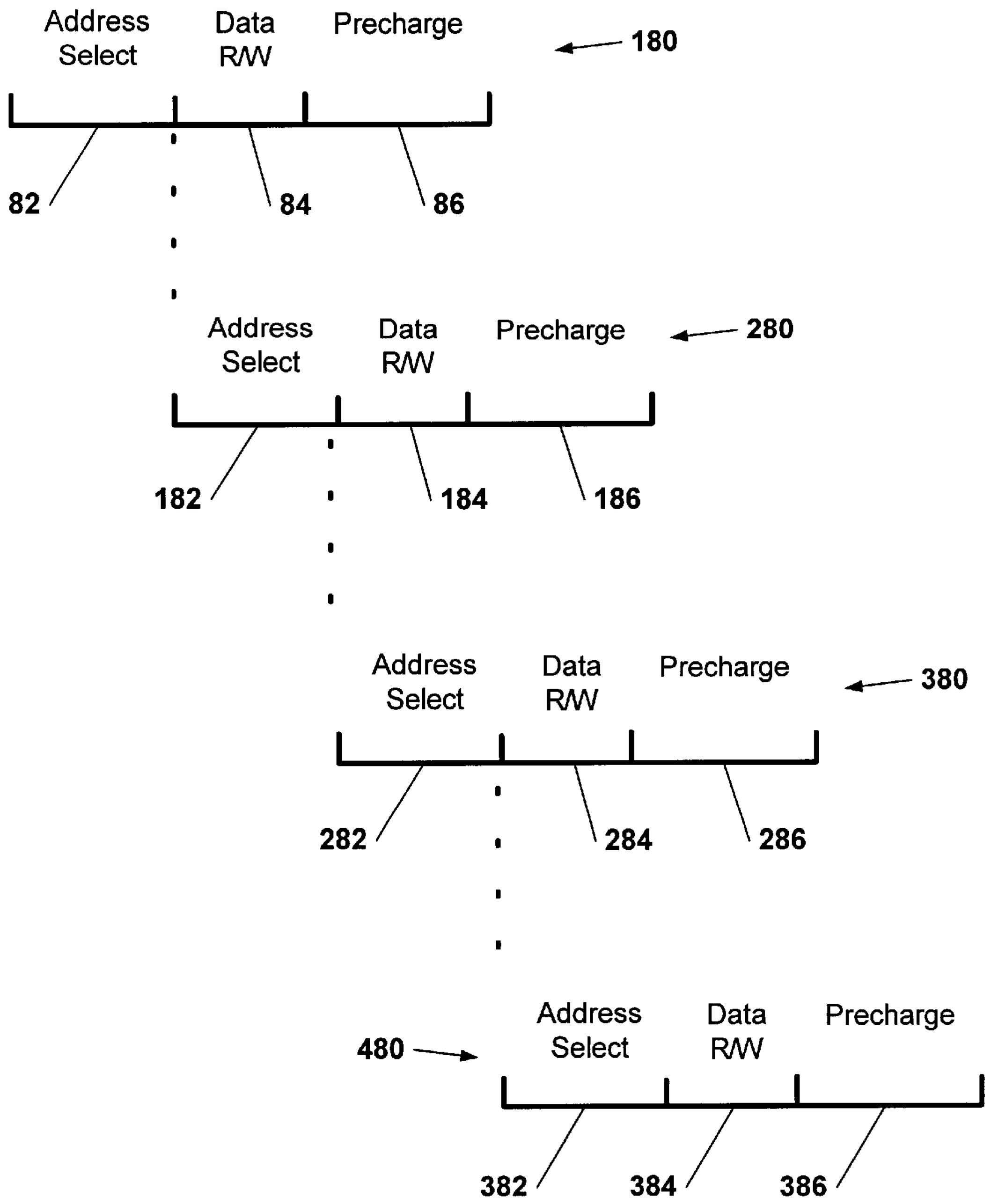
FIGS. 3A, 3B, 3C, and 3D depict timing diagrams for DDR-SDRAM data cycles illustrating improvement of memory access speed, in accordance with an embodiment of the present invention.
Figure 3B:
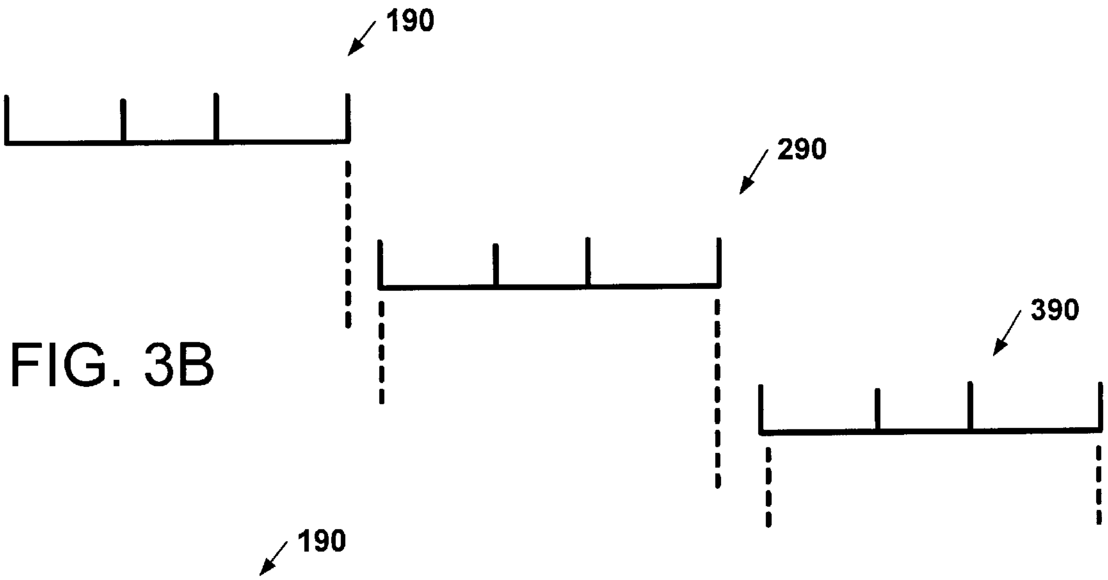
Figure 3C:
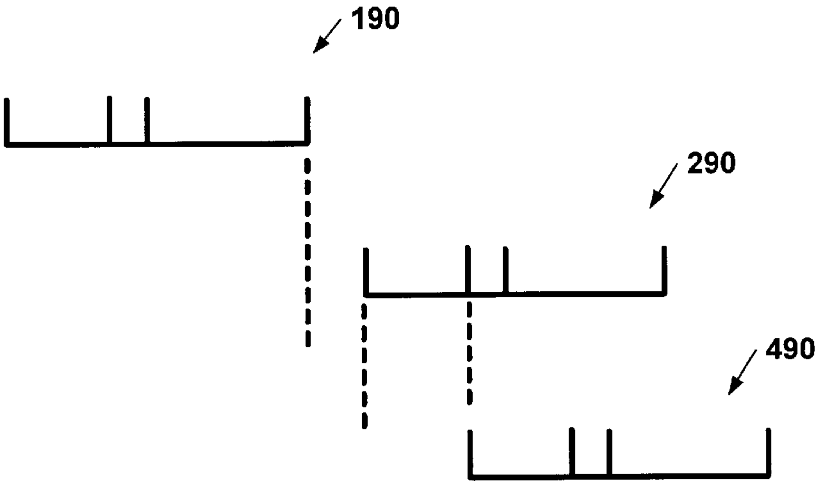
Figure 3D:
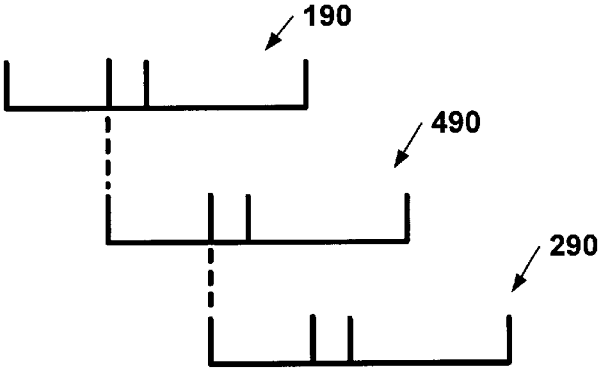

Referring now to FIGS. 3A, 3B, 3C, and 3D, an example is described of optimized timing cycles for the high-density memory 22 and its associated controller 24. It is shown in FIGS. 3B and 3D that a memory bank access sequence of a bank one access followed by a second bank one access can take longer total time to complete than a memory bank access sequence of a bank one access followed by a bank two access followed by a second bank one access. In general this cycle is determined by the operating characteristics of the specific device chosen for high-density memory 22, but in this example, the device 22 is operated optimally as shown in FIG. 3A. Memory cycle 180 is divided into three parts: an address-select period 82, a data read/write period 84, and a teardown/precharge period 86. Memory cycles 280, 380, 480, 190, 290, 390, and 490 are similarly divided.

Consider a previous memory cycle and a current memory cycle. Memory 22 has the operating characteristic that if and only if bank switching occurs between the previous memory cycle and current memory cycle, then the address select for the current cycle is allowed to overlap the read/write period and the teardown/precharge period of the previous memory cycle. Within the scope of the present invention, the exact overlap may vary as appropriate depending on the specific embodiment. Because the memory cycle can begin sooner than it otherwise would, savings in time is achieved, leading to greater efficiency.

FIG. 3A illustrates this operating characteristic of memory 22. In this illustration, memory service requests are pending for all four banks. Memory cycle 280 begins after memory cycle 180, such that memory cycle 280 can overlap with read/write 84 and teardown/precharge 86. Likewise memory cycle 380 begins after memory cycle 280, such that memory cycle 380 can overlap with read/write 184 and teardown/precharge 186. And memory cycle 480 begins after memory cycle 380, such that memory cycle 480 can overlap with read/write 284 and teardown/precharge 286. Other sequences would similarly be possible to exploit this overlap.

The memory controller 24 must also handle cases where there are not service requests pending for all memory banks. A worst case is illustrated in FIG. 3B, where memory cycles 190, 290, and 390 are pending for bank one 122. In this case timing overlap cannot be used, and the controller must use the memory access timing shown in FIG. 3B: components of memory cycles 190, 290, and 390 do not overlap. The lack of overlap is partly mitigated by the fact that the service requests being handled use all of the memory access cycles available, which is the best that can be accomplished within the limitations of the chosen memory device. Within the scope of the present invention, it is obvious that the combinations of various banks, requests, and the efficient ordering of requests cannot be exhaustively listed. The innumerable embodiments of the invention share the efficient use of type one RAM by overlapping memory cycles, and are thus within the scope of the present invention.

There are also intermediate cases between the situations of FIG. 3A and FIG. 3B, and one of these is illustrated in FIG. 3C. In this case a memory service request 190 to bank one 122, a request 290 to bank one 122, and a request 490 to bank two 222 have arrived, in that order. If executed in that order, the timing sequence would be as shown in FIG. 3C, with overlap at only the bank-switching event between memory cycles 290 and 490. However, by reordering the memory cycles, as shown in FIG. 3D, so that access 490 to bank two 222 is interleaved between the accesses 190 and 290 to bank one 122, two overlaps are allowed. The controller 24 recognizes this and similar situations, and reorders the service requests to provide maximal overlap, thus optimizing usage of the memory.

Thus the performance of the entire memory subsystem 20 is optimized by buffering access requests such that channel 26 is fully occupied at every memory access cycle, and by overlapping timing cycles wherever possible by resequencing service requests to force bank switching. In this way, small discontiguous memory service requests from processor clients 130, 230, 330, 430, 530, and 630 can be supported efficiently using high-density memory.

It will be recognized by those skilled in the art that memory service requests will not be executed in the order received by the system described by reference to FIGS. 1 and 2, and this can lead to issues with memory coherency unless further functionality is added to the memory controller 24.

This further functionality can be provided by snapshotting to support the following functions in an embodiment:

1. The controller prioritizes service requests for each memory address such that write requests are always executed before read requests. This ensures that data returned by read requests is always the most recent value at each memory location;
2. Addresses of read requests are compared to pending write requests at that memory address. If a write request is pending at that address, the read request could be filled by the data of the pending write request, thus accelerating the response to read requests.

Further measures may be needed to maintain coherency. For instance, if two clients are exchanging data by sharing memory space, one client may be given write access to only half of the memory space but read access to all, the second client will be given write access to the other half of the memory space and read access to all, thus ensuring that it is known which client has written the contents of each memory location. This level of coherency control is normally not the responsibility of the memory control system.

Figure 4:
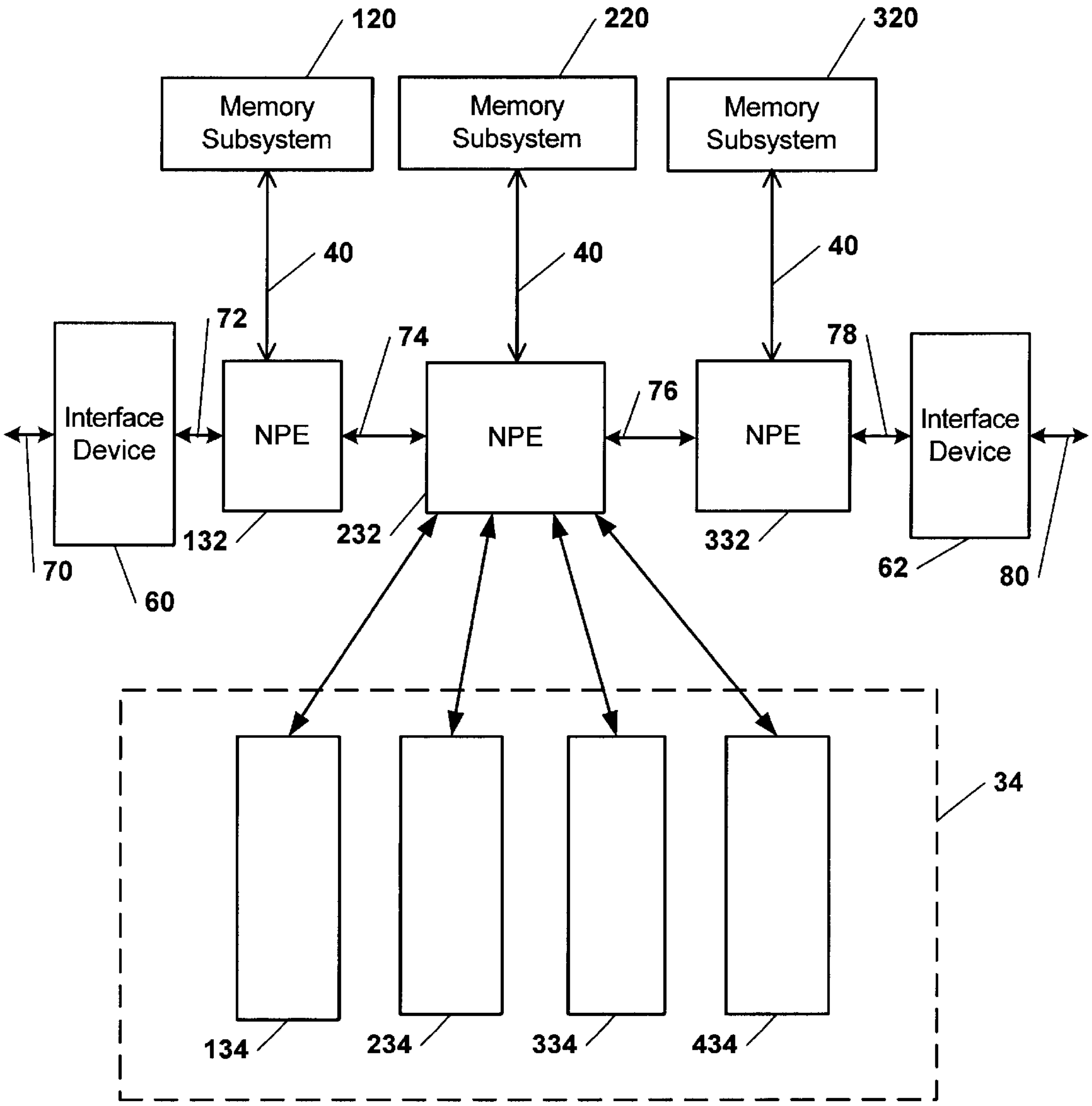
FIG. 4 shows a block diagram of general data connectivity and processing units within a portion of a digital electronic network, in accordance with an embodiment of the present invention.

FIG. 4 shows an example of an in-line networking component using three instantiations of memory subsystem 20. Network processing engines (NPEs) 132 and 332 are respectively connected by bidirectional data channels 72 and 78 to network interface devices 60 and 62. For purposes of the present description the network interface devices 60 and 62 may be considered as functionally equivalent, although in practice they may differ to accommodate different communication protocols for the data channels 70 and 80.

NPEs 132 and 332 respectively connect through NPE 232 using bidirectional data channels 74 and 76. NPE 232 runs a plurality of clients such as 134, 234, 334 and 434 to support network services for NPEs 132 and 332. Clients such as clients 134, 234, 334 and 434 are not necessarily external entities. In this embodiment, clients 134, 234, 334 and 434 are running 34 on NPE 232.

NPEs 132, 232 and 332 are generally similar though they will normally be programmed to provide different functionalities. The NPEs use memory subsystems 120, 220 and 320 that are analogous to memory subsystem 20 described in FIGS. 1, 2, 3A, 3B, 3C, and 3D.

In an embodiment, this is an SSL solution network. Connection 70 would be to the client side, network connection 80 to the server side, and applications 134, 234, 334, and 434 would be the SSL handshake and cryptography processing. In this embodiment, memory 120 would contain the TCP connection information of the client connection and memory 320 would contain the TCP connection information of the server connection. The network processing engines must index into their respective memories to determine the connection for which the current packet belongs as well as gather the state data necessary for further application processing of the packet. The indexing itself could take several individual accesses for large databases that require hash tables rather than a direct lookup. Memory 220 would be used to hold the application data state along with the data to be processed. In order not to burden the connection memories 120 and 320 with bulk data being separately buffered for each connection, the network data can be passed directly to memory 220 for storage and linked together via pointers held by the connection state information. NPE 232 and memory 220 act as the shared memory storage between the network connections and application processing.

In another embodiment, a similar structure can be applied to an IPSec implementation wherein the connection is not TCP but rather the security association that bounds the individual client-to-server session. Another embodiment is a TCP termination offload device where the TCP connection to the client is terminated in NPE 132 to provide a complete in-order data stream to processing elements connected to network connection 80. Here a simpler protocol like UDP may be running on NPE 332. Even though a simpler protocol may be employed on the server end, the requirement for large connection tables still exists and thus the memory requirements still exist.

APPENDIX A—GLOSSARY

This Glossary defines words as they are used throughout this application. This Glossary lists base words rather than word variations. But the meanings of word variations—such as "connecting," "connect," and "connected" for the base word "connection" —are also given meaning according to their logical relationship to the base word.

"=" means equality or congruence, depending on the context. This is clear to typical practitioners of this technical area.

"~" means approximately.

"1K" means 1024.

"2K" means 2048.

"4K" means 4096.

"Φ[Δ]" means Φ's Δ-th bit.

"Φ[Δ:β]" means a binary number composed of the bit sequence of Φ that starts with Φ's Δ-th bit and ends with Φ's β-th bit. For example, if Φ is a 512-bit number, it would typically be represented in its entirety as Φ[511:0]; its highest ten bits would be represented by Φ[511:502].

"Algorithm" means a process for completing a task. An encryption algorithm is the process, typically with mathematical characteristics, to encrypt and decrypt messages.

"ARP" means Address Resolution Protocol. To map an IP address into a hardware address, a computing device uses the ARP protocol which broadcasts a request message containing an IP address, to which a target computing device replies with both the original IP address and the hardware address.

"Asymmetric encryption" means encryption used in a public-private key cryptosystem.

"Asymmetric key cipher" means a public-private key cryptography system.

"Authentication" means the process of verifying that a file or message has not been altered in route from the distributor to the recipient(s).

"Chaining controller" means a controller that associates stations as a computational chain. One example of a chaining controller is the Security Protocol Processor DMA Engine that chains exponentiators into an exponentiation chain.

"Cipher" means a cryptographic algorithm used to encrypt an decrypt files and messages.

"Ciphertext" means the disguised (or encrypted) file or message.

"Computational chain" means two or more stations that are chained together to perform a computation beyond the capacity of a single station.

"Computational device" means a device that is given an input, computes a result based on the input, and outputs the result. A computational device is an example of a computational device.

"Computing device" means a device having at least one processor and at least one memory device, wherein the processor can process data that can be stored in the memory device before and/or after processing, or a group of devices having that capacity in combination. By this definition, examples of a computing device include computer personal computer, palm computing device, notebook computer, server, mainframe, network of computing devices with coordinated processing or storage, network of components functioning together as a computing device wherein any single component may not be a computing device in its own right, etc. As another example, components of a computing device may be connected across the Internet. Other examples of computing devices could include boards, chips, exponentiators, multipliers, etc.

"Connection" means any connection that is adapted to carry communication, whatever the supporting technology. Examples of connections include hard wire connections such as phone lines, T1 lines, DSL, fiber optic, Ethernet, twisted pair, etc. Other examples of connections include wireless connections such as those operating by electromagnetic waves, wireless optics (e.g., infrared), etc. Further examples are a logical connection between two processes on the same system, and a connection between two processes sharing a common memory space.

"Coprime" is defined such that if P and Q are coprime, their greatest common divisor is 1.

"Cryptanalysis" means the art of breaking cryptosystems. It also means the process of looking for errors or weaknesses in the implementation of an algorithm or of the algorithm itself.

"Cryptography" is the art of creating and using cryptosystems.

"Cryptosystem" means the entire process of using cryptography. This includes the actions of encrypting and decrypting a file or message. It also means authenticating the sender of an e-mail message.

"Decryption" means any process to convert ciphertext back into plaintext. Decrypting is synonymous to decoding.

"DDR-SDRAM" means SDRAM that supports data transfers on both edges of each clock cycle (the rising and falling edges). DDR-SDRAM is an abbreviation of Double Data Rate Synchronous DRAM and is also called SDRAM II.

"DES" means the Data Encryption Standard. It is a cipher developed by the United States government in the 1970s to be the official encryption algorithm of the United States.

"Digital signature" means systems that allow people and organizations to electronically certify such features as their identity, their ability to pay, or the authenticity of an electronic document.

"DRAM" means RAM that must be continually refreshed or it will lose its state (on/off). DRAM is an abbreviation for Dynamic RAM and is the most widely used RAM in PCs at this time.

"Encryption" means any process to convert plaintext into ciphertext. Encrypting is synonymous to encoding.

"Exponentiation chain" means two or more stations that are chained together to perform a exponentiation beyond the capacity of a single station.

"Exponentiator" means a computational device that performs exponentiation.

"Fanout" means distributing a signal to multiple destinations.

"FTP" means File Transfer Protocol. FTP enables transferring of text and binary files over TCP connections. FTP allows transferring files according to a strict mechanism of ownership and access restrictions. It is now one of the most commonly used protocols over the Internet.

"Hamming weight" means the number of "1" bits in the binary representation of a number.

"High fanout" means distributing a signal to a great enough number of destinations that a significant delay occurs before all the destinations receive the signal.

"HTTP" means Hyper Text Transfer Protocol. It is a protocol used to transfer hypertext pages across the World Wide Web. "IP" means Internet Protocol, and is the underlying protocol for the other Internet protocols. IP defines the means to identify and reach a target computer on the network. A unique number known as an IP address identifies each computing device in the IP world.

"IPSec" means Internet Protocol Security. It is a standard for security at the network or packet-processing layer of network communication. IPSec provides two choices of security service: Authentication Header (AH), which essentially allows authentication of the sender of data, and Encapsulating Security Payload (ESP), which supports both authentication of the sender and encryption of data. IPSec is a suite of protocols that protect client protocols of EP, such as TCP. IPSec describes mechanisms that provide data source authentication, data integrity, confidentiality and protection against replay attacks. IPSec provides transport mode and tunnel mode operation. Some embodiments provide only tunnel mode operation, and others offers a more complete IPSec implementation.

"iSCSI" is a software package that emulates SCSI protocols, but the connection method is via an IP network instead of a direct SCSI compatible cable. This is one example of IP-based storage.

"Key" means a collection of bits, usually stored in a file, which is used to encrypt or decrypt a message.

"Network protocol" means a standard designed to specify how computers interact and exchange messages. It usually specifies the format of the messages and how to handle errors. The following Internet protocols are examples of network protocols: ARP, FTP, HTTP, IP, NNTP PPP, SLIP, SMTP, SNMP, TCP, Telnet, and UDP.

"NNTP" means Network News Transfer Protocol. It is a protocol used to carry USENET postings between News clients and USENET servers.

"PGP" means Pretty Good Privacy. It is a public-private key cryptosystem that allows users to more easily integrate the use of encryption in their daily tasks, such as e-mail protection and authentication, and protecting files stored on a computer. PGP is available for free to individual home users.

"Plaintext" means the original message or file. After a file or message has been encrypted and then decrypted you should end up with the original file or message.

"PPP" means Point-To-Point protocol, and is a protocol for creating a TCP/IP connection over both synchronous and asynchronous systems. PPP provides connections for host-to-network or router-to-router. It also has a security mechanism. PPP is well known as a protocol for connections over regular telephone lines using modems on both ends. This protocol is widely used for connecting personal computers to the Internet.

"Private key" means the private key of a public-private key cryptosystem. This key is used to digitally sign outgoing messages and is used to decrypt incoming messages.

"Public key" means the public key of a public-private key cryptosystem. This key is used to confirm digital signatures on incoming messages or to encrypt a file or message so that only the holder of the private key can decrypt the file or message.

"Public key cryptosystem" means an asymmetric encryption algorithm in which it is infeasible to derive one key from the other.

"Public-private key cryptosystem" means a cryptosystem that uses two different keys to encrypt and decrypt messages and files. The two keys are mathematically related to each other, but deriving one key from the other is infeasible. One key is a public key and one key is a private key. The public key is usually distributed to other users, and the private key is usually kept secret.

"RAM" means computer memory that can be accessed randomly. Data can be read from or written to any portion of RAM, regardless of its position. RAM is an abbreviation for Random Access Memory.

"Replicating fanout logic" means distributing mirrored state information so that multiple controllers can operate based on the same state information without delay based on a high fanout.

"Ring arithmetic" means an arithmetic of mathematical structures in which addition, subtraction, multiplication, and their obvious consequences such as exponentiation, have the properties and interrelationships usually encountered in high school algebra.

"RSA exponentiation" means the process for both encryption and decryption in the RSA public-key process. It entails the computation of $A^b$ mod m, where b and m are elements of the key and A is the data to be encrypted or decrypted.

"RSA session" means a session launched by an exponentiator to compute an exponentiation.

"SCSI" is an intelligent protocol that enables data blocks to be read at high speed from or sent at high speed to storage devices such as disks or tape drives. Early implementations of SCSI used ribbon cable and industry standard logic levels.

"SDRAM" means DRAM that has its operations synchronized to an external clock. SDRAM is an abbreviation for Synchronous DRAM.

"Security association" means a relationship between two or more entities that describes how the entities will utilize security services to communicate securely. This relationship is represented by a set of information that can be considered a contract between the entities. The information must be agreed upon and shared between all the entities. Security association is commonly abbreviated SA.

"Shotgun multiplication" means a process like that described in this application for performing fast computations by performing processing in mathematically independent units, taking advantage of more than one basis and precomputed operands, and accommodating iterative problems.

"SLIP" means Serial Line Internet Protocol, and is a point-to-point protocol to use over a serial connection, a predecessor of PPP. There is also an advanced version of this protocol known as CSLIP (compressed serial line internet protocol) that reduces overhead on a SLIP connection by sending just header information when possible, thus increasing packet throughput.

"SMTP" means Simple Mail Transfer Protocol, and is dedicated to sending e-mail messages originating on a local host to a remote server over a TCP connection. SMTP defines a set of rules that allows two programs to send and receive e-mail over the network. The protocol defines the data structure to deliver with information regarding the sender, the recipient(s) and the e-mail's body.

"Snapshotting" means recording the present state of potentially changing values so that the values can be treated as fixed.

"SNMP" means Simple Network Management Protocol. It is a simple protocol that defines messages related to network management. Through the use of SNMP, network devices such as routers can be configured by any host on their network.

"SRAM" means RAM that is generally faster at accessing random data than DRAM. But at this time SRAM is more expensive and requires more power. SRAM is an abbreviation for Static RAM.

"SSL" means Secure Sockets Layer, and is a trademark of Netscape. It is a program layer created by Netscape for managing the security of message transmissions in a network. The concept is that the programming for keeping messages confidential is to be contained in a program layer between an application (such as a Web browser or HTTP) and the Internet's TCP/IP layers. The "sockets" part of the term refers to the sockets method of passing data back and forth between a client and a server program in a network or between program layers in the same computer.

"SSL/TLS" means compatible with SSL and with TLS.

"Symmetric key" means the key of a symmetric key cryptosystem. The symmetric key is used to encrypt a file or message and also to decrypt the file or message.

"Symmetric key cryptosystem" means a cryptosystem that uses one key to lock and unlock—encrypt and decrypt—messages and files. The sender must posses the key to encrypt a file or message, and the recipient(s) must possess the key to decrypt the file or message.

"TCP" means Transmission Control Protocol. Like UDP, TCP is a protocol that enables a computer to send data to a remote computer. But unlike UDP, TCP is reliable —packets are guaranteed to wind up at their target in the correct order.

"Telnet" is a terminal emulation protocol for use over TCP connections. It enables users to login to remote hosts and use their resources from the local host.

"TLS" means Transport Layer Security. It is the successor protocol to SSL, created by the Internet Engineering Task Force (IETF) for general communication authentication and encryption over TCP/IP networks. TLS version 1 is nearly identical with SSL version 3, providing data integrity and privacy on a communications link over the Internet. It allows client-server applications to communicate and is designed to prevent eavesdropping, message forgery, and interference.

"TOE" means TCP Offload Engine. TOE technology typically takes the server CPU out of I/O processing by shifting TCP/IP processing tasks to a network adapter or storage device. This leaves the CPU free to run its applications, so users get data faster.

"Triple DES" means a method of improving the strength of the DES algorithm by using it three times in sequence with different keys.

"UDP" means User Datagram Protocol. It is a simple protocol that transfers datagrams (packets of data) to a remote computer. UDP doesn't guarantee that packets will be received in the order sent or that they will arrive at all.

"Wire speed" means the rate of data transfer a given telecommunication technology provides at the physical wire level. Wire speed also means any equipment or function that tends to support this data transfer rate without slowing it down. It is common to refer to functions embedded in microchips rather than in software programming as working at wire speed. Some switches, routers, and other devices operate at, or close to, wire speed. Some encryption, decryption, hardware emulation, and other software functions operate at, or close to, wire speed when embedded in a microchip.

Any element in a claim that does not explicitly state "means for" performing a specified function, or "step for" performing a specific function, is not to be interpreted as a "means" or "step" clause as specified in 35 U.S.C. § 112, ¶6. In particular, the use of "step of" in the claims herein is not intended to invoke the provision of 35 U.S.C. § 112, ¶6.

It should be apparent from the foregoing that an invention having significant advantages has been provided. While the invention is shown in only a few of its forms, it is not just limited to those forms but is susceptible to various changes and modifications without departing from the spirit thereof.

What is claimed is:

1. A RAM device comprising:

a memory; and a memory controller, wherein the memory controller is configured to:

buffer a plurality of incoming requests;

prioritize the incoming requests into a final order, as needed, to maximize overlap of incoming requests' timing cycles; and submit the incoming requests to the memory in the final order;

wherein the memory includes a first bank and a second bank;

wherein the memory controller is configured to fulfill a first request, directed to the first bank, by accessing the first bank via a first memory cycle;

wherein the memory controller is configured to fulfill a second request, directed to the first bank, by accessing the first bank via a second memory cycle;

wherein the memory controller is configured to fulfill a third request, directed to the second bank, by accessing the second bank via a third memory cycle;

wherein submitting the first request, the second request, and the third request in that first order results in a first delay; and wherein submitting the first request, the third request, and the second request in that second order results in a second delay totaling less than the first delay.

2. The device of claim 1, wherein the memory controller received the first, second, and third requests in that order; and wherein the memory controller is configured to submit the requests in the second order.

3. The device of claim 1, wherein the memory controller is configured to buffer the first request, the second request, and the third request;

wherein the memory controller is configured to prioritize request submission so that adjacently submitted requests are directed to different banks as possible.

4. The device of claim 3, wherein the memory controller comprises:

a first buffer;

a second buffer;

a third buffer;

wherein the contents of only one buffer at a time may be communicated to the memory.

5. A RAM device comprising:

a memory, and a memory controller, wherein the memory controller is configured to:

buffer a lurality of incoming requests;

prioritize the incoming requests into a final order, as needed, to maximize overlap of incoming requests' timing cycles; and submit the incoming requests to the memory in the final order;

wherein if the memory controller submits a first request before a second request, both requests will be fulfilled before the end of a first delay;

wherein if the memory controller submits the second request before the first request, both requests will be fulfilled before the end of a second delay;

wherein the second delay is shorter than the first delay;

wherein the memory controller is configured to prioritize the second request before the first request responsively to ascertaining that the second request should be submitted before the first request; and wherein the memory controller submits the second request before the first request.

6. The device of claim 5, wherein the memory controller is configured to buffer the first request and the second request and only one of the two requests can be submitted to the memory at a time.

7. A RAM device comprising:

a memory; and a memory controller, wherein the memory controller is configured to:

buffer a plurality of incoming requests;

prioritize the incoming requests into a final order, as needed, to maximize overlap of incoming requests' timing cycles; and submit the incoming requests to the memory in the final order;

wherein the memory controller is configured to fulfill a first request via a first memory cycle;

wherein the memory controller is configured to fulfill a second request via a second memory cycle;

wherein the memory controller is configured to fulfill a third request via a third memory cycle;

wherein if the first request is a read and if the second request is a write and if the third request is a read, then submitting the first request, the second request, and the third request in that first order results in a first delay; and submitting the first request, the third request, and the second request in that second order results in a second delay totaling less than the first delay; and wherein if the first request is a write and if the second request is a read and if the third request is a write, then submitting the first request, the second request, and the third request in that third order results in a third delay; and submitting the first request, the third request, and the second request in that fourth order results in a fourth delay totaling less than the third delay.

8. The device of claim 7, wherein the memory controller received the first, second, and third requests in the first order; and wherein the memory controller is configured to submit the requests in the second order.

9. The device of claim 7, wherein the memory controller received the first, second, and third requests in the third order; and wherein the memory controller is configured to submit the requests in the fourth order.

10. The device of claim 7, wherein the memory controller is configured to buffer the first request, the second request, and the third request;

wherein the memory controller is configured to prioritize request submission so that read requests are adjacent to read requests and so that write requests are adjacent to write requests as possible.

* * * * *

UNITED STATES PATENT AND TRADEMARK OFFICE

CERTIFICATE OF CORRECTION

PATENT NO. : 6,738,874 B2
DATED : May 18, 2004
INVENTOR(S) : Leslie Zsohar

It is certified that error appears in the above-identified patent and that said Letters Patent is hereby corrected as shown below:

Column 14,
Line 53, cancel "a memory, and" and insert the following: -- a memory; and --
Line 56, cancel "buffer a lurality of incoming requests;" and insert the following: -- buffer a plurality of incoming requests; --

Signed and Sealed this

Twentieth Day of July, 2004

JON W. DUDAS
*Acting Director of the United States Patent and Trademark Office*